United States Patent
Contractor et al.

(10) Patent No.: US 6,310,240 B1
(45) Date of Patent: Oct. 30, 2001

(54) VAPOR PHASE OXIDATION OF ACROLEIN TO ACRYLIC ACID

(75) Inventors: Rashmikant Maganlal Contractor, Wilmington, DE (US); Mark William Andersen, Charlottesville, VA (US); Daniel Campos, Wilmington, DE (US); Gerard Hecquet, Courbevoie (FR); Charlotte Pham, Saverne (FR); Michel Simon, St. Avold (FR); Mireille Stojanovic, Paris (FR); Roland Kotwica, Pontpoint (FR); Jean-Pierre Schirmann, Oullins (FR)

(73) Assignees: E. I. du Pont de Nemours and Company, Wilmington, DE (US); Atofina, Puteaux (FR)

( * ) Notice: Subject to any disclaimer, the term of this patent is extended or adjusted under 35 U.S.C. 154(b) by 0 days.

(21) Appl. No.: 09/219,944

(22) Filed: Dec. 23, 1998

(51) Int. Cl.$^7$ .................................................. C07C 51/235
(52) U.S. Cl. .............................................................. 562/535
(58) Field of Search ............................................. 562/535

(56) References Cited

U.S. PATENT DOCUMENTS

| | | |
|---|---|---|
| 4,092,354 | 5/1978 | Shiraishi et al. ..................... 260/530 |
| 4,668,802 * | 5/1987 | Contractor . |
| 4,677,084 | 6/1987 | Bergna ..................................... 502/8 |
| 4,769,477 | 9/1988 | Bergna ................................... 549/259 |
| 5,646,305 * | 7/1997 | Wagner et al. . |
| 6,025,523 | 2/2000 | Hecquet et al. ..................... 562/535 |
| 6,107,238 | 8/2000 | Contractor et al. .................. 502/247 |

FOREIGN PATENT DOCUMENTS 3-170445   7/1991   (JP) .

OTHER PUBLICATIONS

Dupont Technology Transfer, Advertising Chemicals Technologies Worldwide, 1973.

* cited by examiner

*Primary Examiner*—Paul J. Killes
*Assistant Examiner*—Robert W. Deemie

(57) ABSTRACT

An improved method for the selective vapor phase oxidation of acrolein to acrylic acid in a recirculating solids reactor system using a particulate molybdenum vanadate multimetal oxide as oxidant involving specific reactant concentrations (preferably 5 mol % to 30 mol % propylene, 0 to 20 mol % oxygen, 0 to 70 mol % water, and the remainder inert gas), solids particle size (20 to 300 micrometers), temperature (250 to 450° C.) and gas (1 to 15 seconds) and solids (2 to 60 seconds) residence times. Such a process leads to improved selectivity, conversion and solids conversion ratio.

6 Claims, 2 Drawing Sheets

US 6,310,240 B1

VAPOR PHASE OXIDATION OF ACROLEIN TO ACRYLIC ACID

BACKGROUND OF THE INVENTION

1. Field of the Invention

The present invention relates to an improved vapor phase process for the oxidation of acrolein to acrylic acid using as oxidant particulate molybdenum vanadate multimetal oxide in an oxidized state, and wherein the resulting reduced solids are separately regenerated using molecular oxygen. More specifically but not by way of limitation, the invention relates to a process for performing this reaction in a recirculating solids reactor system.

2. Description of the Related Art

An important route to acrylic acid is the vapor phase oxidation of acrolein over a multicomponent catalyst containing molybdenum, vanadium and/or other metals, usually as their oxides. The reaction step involves oxidation of acrolein with air (oxygen) to form acrylic acid, along with carbon oxides, water and smaller amounts of other oxidized byproducts. Preferably, the feed gas also contains steam. Typically the reaction is carried out in multitubular fixed-bed reactors. The large exothermic heat of reaction and the thermal sensitivity of the acrolein oxidation requires low feed concentrations, expensive heat transfer equipment, handling of a large volume of gas, and good reactor temperature control. Low acrolein concentration is also required to avoid flammability conditions.

The magnitude of some of these problems is reduced when a fluidized-bed reactor is used. The temperature can be readily controlled within a few degrees because of the intensive solids mixing and the good heat transfer characteristics. Higher acrolein concentrations can be used because the danger of flammability is reduced by introducing the acrolein directly into the reactor rather than premixing it with air (oxygen). However, very high acrolein concentrations and low oxygen-to-acrolein ratios in the reactor may result in the over reduction of the solids and reduced selectivity to acrylic acid. Also, significant back-mixing of gases in the fluidized-bed reactor result in selectivity losses.

Modified forms of fluidized-bed reactor which minimize back-mixing are known as recirculating solids reactor, transport bed reactor, transport line reactor, riser reactor, fast fluidization reactor, multi-chamber fluidized bed reactor, and by other names, depending on design and/or personal preference. In this application we will use the term "transport bed reactor" to mean any reactor in which solid particles are injected at one end of the reactor and carried along with gas reactants at high velocities and discharged at the other end of the reactor to a gas-solids separation vessel. A riser reactor, in which the reactor is a vertical pipe wherein the active solids and gases are fed in at the bottom, transported in essentially plug flow and removed at the top, is one example of a transport bed reactor. Another example is a pipeline reactor, in which the flow of active solids and gases is other than vertically upwards. A transport bed reactor, as defined herein, includes a riser reactor or pipeline reactor which also incorporates a zone for fluidization, i.e., a zone where the gas velocities are sufficiently high to carry out a substantial portion of the active solids fed, but with more back-mixing of active solids than would occur in plug flow. We will use the term "recirculating solids reactor system" to mean a general reaction system with two reaction zones, in which two separate reactions take place, and which uses a particulate solid which circulates between the two reaction zones and takes part in both reactions. Optionally, either or both reaction zones may involve either a transport bed reactor or a fluidized bed. Such reaction systems have found use in catalytic cracking in petroleum refining and in other reactions.

U.S. Pat. No. 4,668,802 discloses a process for preparing maleic anhydride by oxidizing butane using an oxidized vanadium-phosphorous oxide catalyst as oxidant rather than oxygen wherein the resulting reduced catalyst is separately regenerated, and the use of a recirculating solids reactor system for this reaction. Certain of the examples use a transport bed or riser reactor for the butane oxidation reaction.

Japanese Kokai 3-170,445 discloses a similar process for preparing a mixture of acrolein and acrylic acid by oxidizing propane using an oxidized bismuth-molybdenum catalyst or vanadium pyrophosphate catalyst as oxidant.

An advertising folder prepared by E. I. DuPont in 1973 titled "Chemical Technologies Worldwide" included a single sheet titled "Transport Bed Reactor Technology for Selective Processes", which described the general advantages of a transport bed or riser reactor, listing among typical applications the reaction of propylene to make acrylic acid.

The preparation of multicomponent compositions containing molybdenum and/or other metals and their use as catalysts in the oxidation of acrolein to make acrylic acid is well known in the art. For example, numerous patents such as U.S. Pat. No. 4,092,354 disclose specific compositions containing molybdenum and vanadium for use in the oxidation of acrolein to acrylic acid in a vapor phase oxidation using molecular oxygen. U.S. Pat. No. 4,677,084 discloses a process for making highly attrition resistant silica-based catalysts containing molybdenum, vanadium or other metals.

None of the above references disclose the necessary information to enable the economical use of a vapor phase process for the oxidation of acrolein to acrylic acid using as oxidant a solid in an oxidized state, and where the resulting reduced solid is separately regenerated using molecular oxygen.

BRIEF SUMMARY OF THE INVENTION

The present invention relates to an improved process for the selective vapor oxidation of acrolein to acrylic acid in a recirculating solids reactor system using a molybdenum vanadate multimetal oxide in an oxidized form or state as the oxidant. Thus the present invention provides a process for the oxidation of acrolein to acrylic acid comprising the steps of:

(a) contacting a feed gas containing from 1 mol % to 100 mol % acrolein, 0 to 20 mol % oxygen, 0 to 70 mol % water, and the remainder inert gas with an effective amount of an oxidant comprising a particulate molybdenum vanadate multimetal oxide in oxidized form and having a particle size range of 10 to 300 micrometers, in a transport bed reactor at a temperature of about 250 to about 450° C., with a gas residence time in the reaction zone from 1 second to 15 seconds, and with a solids residence time in the reaction zone from 2 seconds to 120 seconds;

(b) removing and recovering acrolein from the effluent gases produced in the transport bed reactor of step (a) by separating the resultant reduced particulate molybdenum vanadate multimetal oxide from the effluent gases;

(c) transporting the reduced particulate molybdenum vanadate multimetal oxide to a regenerator zone of the recirculating solids reactor system;

(d) oxidizing the reduced particulate molybdenum vanadate multimetal oxide in the regenerator zone using an oxygen containing gas, at a temperature of from 250 to 500° C. at a solids residence time in the regenerator zone of from 0.5 minute to 10 minutes, and at an oxygen-containing gas residence time of from 3 seconds to 30 seconds; and (e) recycling the oxidized particulate molybdenum vanadate multimetal oxide from step (d) to the transport bed reactor.

Preferably the feed gas contains from 5 to 30 mol % acrolein. In one particular embodiment of the present invention the contacting of the feed gas and the particulate oxidant mixture in an oxidized state such as to convert the acrolein to acrylic acid is performed in a transport bed reactor of a recirculating solids reactor system. Also, the superficial gas velocity in the riser is maintained at 1 to 10 meters/sec, the solids flux (mass flow rate per unit area) is at 5 to 1,000 $kg \cdot m^{-2} \cdot sec^{-1}$, and the solids regenerator zone is a fluidized bed wherein the oxygen-containing gas to the regenerator is air.

It is an object of this invention to provide an improved vapor phase process using a transport bed reactor for the oxidation of acrolein to acrylic acid using the oxidized form of attrition resistant multimetal oxide, and where the resulting reduced solids are separately regenerated using oxygen containing gas. It is a further object of the present invention to provide a mixed multimetal oxide system that will serve as an oxidant for the vapor phase conversion of acrolein to acrylic acid. Fulfillment of these objects and the presence and fulfillment of additional objects will become apparent upon complete reading of the specification and attached claims.

DETAILED DESCRIPTION OF THE INVENTION

Figure 1:
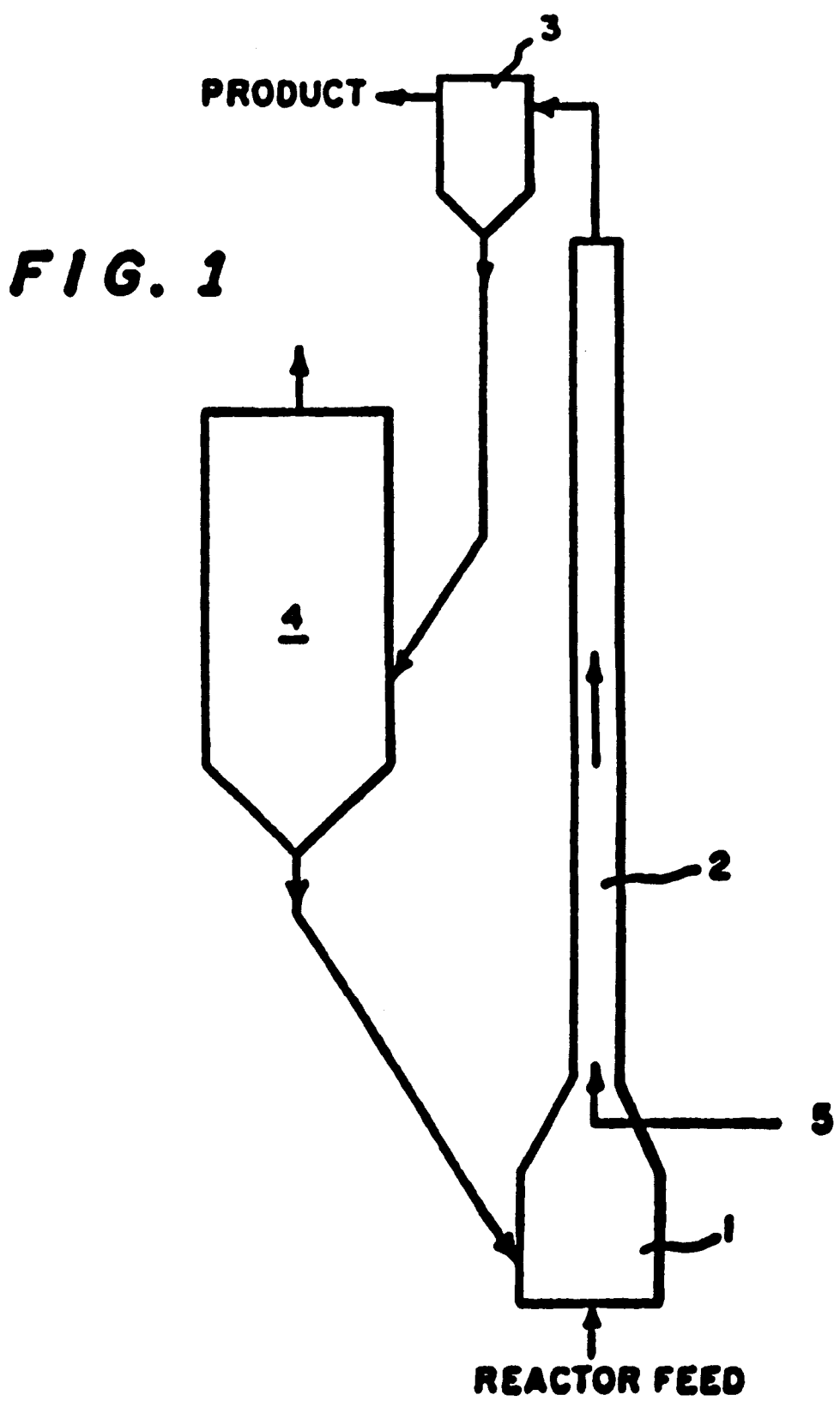
FIG. 1 shows a schematic drawing of a recirculating solids reactor configuration in which the reaction zone is comprised of two parts, a fluid bed section and a riser section and the regeneration zone is comprised of a fluid bed section.

The present invention relates to an improved process for the selective vapor oxidation of acrolein to acrylic acid in a recirculating solids reactor system which includes a transport bed reactor and a separate regenerator. The transport bed reactor is preferably a riser reactor in which particles are injected at the bottom of a vertical pipe, carried upwards with gas reactants at high velocities and discharged to a gas-solids separation vessel, or a combination of a riser reactor with a fluidization zone. The reaction between gas and solids occurs in the riser pipe in a matter of seconds, as distinguished from a conventional fluidized bed reactor where the reaction time is a matter of minutes. Gas velocities in a riser reactor are about 2 to 15 times higher than in fluidized bed reactors; solids concentrations may be up to about 40 times lower. The product of the above reaction is then sent to a conventional processing unit where the acrylic acid is separated and unreacted acrolein is returned for further processing.

The reduced solids are then reoxidized in a separate oxidation step to enable their reuse for the oxidation of acrolein. The reduced solids from the riser zone are first separated from the product gas, stripped of any carbonaceous species in a separate stripper zone and then sent to the regenerator for reoxidation. This process permits independent control of the reactant gas concentrations, the gas residence time, and the solids residence time in each zone for optimum operation.

There are several advantages of the above reactive concept over the steady-state fixed bed or fluidized bed alternative. High selectivity is achieved because of plug flow and optimum oxidative state of the solids. Significant reductions are realized in product recovery costs because the regeneration off-gas stream is kept separate from the product gas stream, resulting in a highly concentrated product stream. High throughput rates are attributed to the independent control of variables for the two steps of the operation, resulting in reduced investment and decreased multimetal oxide inventory.

When a hydrocarbon oxidation reaction is carried out in the absence of molecular oxygen, lattice oxygen from the surface layers of these mixed metal oxide solids gets consumed very rapidly, typically in a matter of seconds. When that occurs, the activity of the solids decreases dramatically. If the solids are allowed to remain in the reducing atmosphere, reduced surface layers are built up on an oxidized core because diffusion of the bulk lattice oxygen to the surface is generally very slow in most practical situations. These reduced layers decrease selectivity and cause excessive yield losses when they get oxidized in the regenerator to carbon oxides. Previous proposals for the oxidation of acrolein to acrylic acid using an oxidant and a separate regeneration zone for the active solids do not disclose the surprising benefit of a short residence time in the acrolein oxidation/solids reduction zone.

In carrying out the inventive process, the feed gas to the acrolein oxidation step contains about 1 mol % to 100 mol % acrolein (preferably about 5 mol % to about 30 mol % acrolein). Some of the acrolein used in the feed may be provided by the unconverted acrolein which is present in the recycled reaction gas. In some cases, acrolein may be available as the predominant component in a mixture of gases including other hydrocarbons. In particular, the mixture of gases may contain amounts of propylene or propane, resulting from their use in the manufacture of acrolein. The oxygen concentration in the feed gas can be from 0 to 20 mol %. Air can be used as the source of oxygen. The remainder of the feed can be any inert gas, such as nitrogen or recycled reaction gas containing mostly water, carbon monoxide and carbon dioxide, and possibly unconverted acrolein.

The present invention uses an effective amount a molybdenum vanadate metal oxide in oxidized form. Preferably these are specially hardened solids which resist attrition, such as disclosed in previously referenced U.S. Pat. Nos. 4,677,084 and 4,769,477 or copending U.S. patent application Ser. No. 09/163,680 filed Sep. 30, 1998 now U.S. Pat. No. 6,107,238. Numerous other molybdenum vanadate metal oxide compositions are disclosed in the art for the vapor phase oxidation of acrolein to acrylic acid, and are also suitable for the operation of this invention. The solid particles are preferably about 10 to about 300 micrometers in size.

The oxidation step is carried out in the reaction zone at a temperature of about 250 to about 450° C. The reactor gas exit pressure is typically 0 to 50 psig (0 to $3.95 \times 10^5$ Pa). The gas residence time in the reaction zone is typically about 1 second to about 15 seconds, and the solids residence time in the reaction zone is about 2 seconds to 120 seconds. The upper limit of solids residence time will, of course, depend on their activity. If still active, the solids can be retained in the reaction zone for longer than 120 seconds. Preferably, the solids are removed from the acrolein oxidation step when the oxidative surface layer of the solids has been essentially reduced to a non-oxidized form. The solids in the reactor effluent are separated from the effluent gases, and the residual acrolein and acrylic acid products are recovered from the effluent gases, both separations employing conventional techniques and equipment. The separated solids are referred to herein as the reduced solids because they are in a lower oxidation state than that of the fresh solids which enters the reaction zone. When appropriate to the embodiment, the reduced solids are preferably stripped of any reactor gases and then transported to the regeneration zone of the recirculating solids reactor system. The stripped reactor gases are mixed with the reactor effluent gases. Acrylic acid is recovered from the effluent gases of the reaction zone in conventional processing units, and remaining gases may be vented or recycled to the reaction zone. Any off-gases from the regeneration zone can be vented preferably after heat recovery.

The reduced solids are reoxidized in the regeneration zone using an oxygen-containing gas such as air, oxygen enriched air or the like. Preferably the regeneration zone temperature is maintained at about 250 to about 500° C. The solids residence time in the regenerator zone is about 0.5 minute to, typically, about 10 minutes. The oxygen-containing gas residence time is about 3 seconds to about 30 seconds. Total gas flow rate and oxygen concentration must be sufficient to provide the needed oxygen for solids reoxidation to occur within the selected gas and solids residence time. The oxidized solids are then recycled to the reaction zone.

The required amount of solids and the required solids circulation rate depend on the extent to which the solids reoxidation reaction is carried out in the regeneration zone (as opposed to the reaction zone), the amount of acrolein to be reacted, the amount of mobile (or reactive) oxygen contained by the solids, and the reaction zone process conditions that determine the amount of oxygen used per pass. When oxygen concentration in the reaction zone is low, or zero, and substantially all of the solids reoxidation reaction is carried out in the regeneration zone, a high solids circulation rate is required. This rate may be reduced, to the extent that the solids reoxidation reaction is carried out in the reaction zone.

A recirculating solids reactor system can be operated continuously to oxidize acrolein without any gas-phase oxygen in the reaction zone. Such operation results in a higher selectivity to make acrylic acid than can be attained with conventional fluidized or fixed bed reactors, providing an adequate solids circulation rate is maintained to supply the needed oxidized solids. In order to minimize the gas phase oxygen in the reaction zone, gas phase oxygen is stripped from the oxidized solids before recycling them to the reaction zone.

Alternatively, if a recirculating solids reactor system is operated so as to oxidize acrolein under conditions of temperature, oxygen and acrolein partial pressures and residence time in the reaction zone identical to those used in conventional reactors, significantly higher conversion of acrolein and significantly higher yield of acrylic acid are obtained.

The high selectivity to acrylic acid attained in the transport bed reactor is maintained even if the feed to the reaction zone has a very high acrolein concentration. The gas feed can be 100% acrolein.

Recirculating solids reactor systems can in general have many different reactor/regenerator configurations. For example, the reaction zone of the system can be comprised of a transport bed reactor, a fluidized bed reactor or other gas-solid reactors, as can the regeneration zone. The recirculating solids reactor system employed in this invention utilizes a transport bed reactor for the reaction zone. Optionally the transport bed reactor may comprise a riser reactor, a pipeline reactor, or a riser or pipeline reactor combined with a fluidization zone. The regeneration zone of the regenerator can be comprised of a riser reactor, a pipeline reactor, a fluidized bed reactor of any type, or a combination of the above reactors. It is to be understood that the invention is not limited to the specific combination of reactors listed above.

A transport bed reactor is characterized by high gas velocities of from about 5 ft/sec (about 1.5 m/sec) to greater than 40 ft/sec (12 m/sec). At the lower end of the velocity range there can be a significant amount of local back-mixing of solids. Typically, the reactor line is vertically mounted with gas and solids flowing upward in essentially plug flow; i.e., a riser reactor. Preferably, the superficial gas velocity in the riser is maintained at 3 to 30 feet/sec (1 to 10 meters/sec). The flow can also be downward and the reactor line can be mounted other than vertically; i.e., a pipeline reactor.

The solids concentration in the reaction zone of the reactor can range from, typically, about 1 lb/ft$^3$ (16 kg/m$^3$) to, typically, about 40 lb/ft$^3$ (640 kg/m$^3$), depending on the gas velocity, solids particle size and density, and the solids circulation rate. Preferably, the solids flux (mass flow rate per unit area) is at 2.1 to 42 lbs·ft$^{-2}$·sec$^{-1}$ (10.2 to 204 kg·m$^{-2}$·sec$^{-1}$).

FIG. 1 is a schematic drawing of one of the recirculating solids reactor systems used in the example. The reaction zone is comprised of a fluidization section 1 and a riser section 2. The feed gas enters 1 and the oxidation of propylene takes place in sections 1 and 2. The separator-stripper unit 3 separates and strips off the reaction zone effluent gases from the reduced solids. The acrylic acid product is recovered from the reactor effluent gases leaving 3. The reduced solids is transported to the regeneration zone which is comprised of the fluidized bed section 4. The reduced solids are oxidized in section 4 and the oxidized (regenerated) solids are then recycled to the fluidization section 1. The alternate/additional feed line 5 can be used to feed additional oxygen or oxygen containing gas, acrolein, or recycle gases to riser section 2. The recirculation solids reactor of this embodiment can also be operated with just the riser section 2 as the reaction zone. In this mode of operation the feed can be introduced into the riser section 2 through feed line 5.

Figure 2:
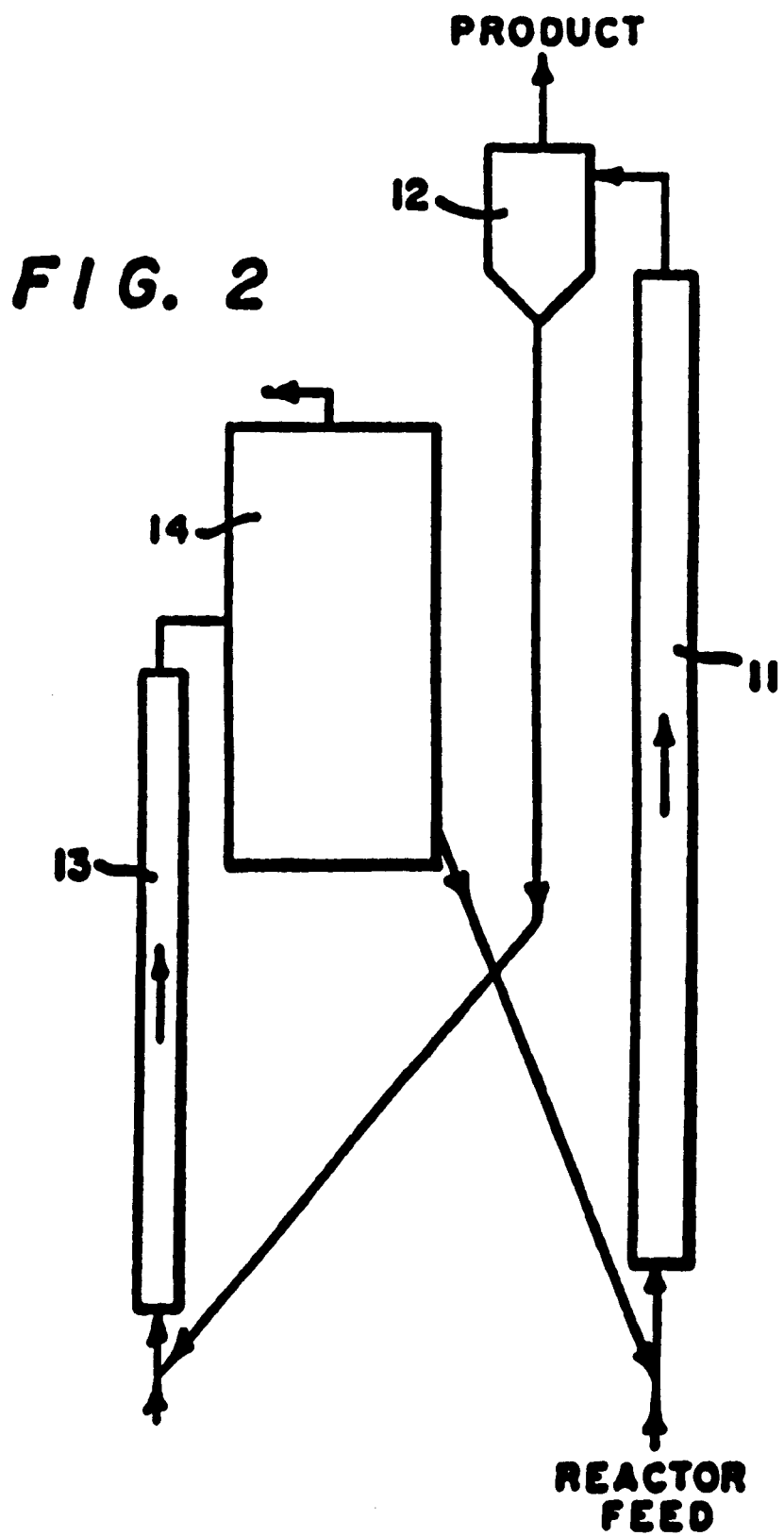
FIG. 2 is shows a schematic drawing of a recirculating solids reactor configuration in which the reaction zone is comprised of a riser section and the regeneration zone is comprised of two parts, a riser section and a fluid bed section.

FIG. 2 is a schematic drawing of another recirculating solids reactor system. The reaction zone is comprised of a riser section 11. The feed gas enters 11 and the oxidation of acrolein takes place in 11. The separator-stripper unit 12 separates and strips off the reaction zone effluent gases from the reduced solids. The acrylic acid product is recovered from the reactor effluent gases leaving 12. The reduced solids are transported to the regeneration zone which is comprised of a riser section 13 and a fluidized bed section 14. The reduced solids are oxidized in this regeneration zone and the oxidized (regenerated) solids are then recycled to the riser section 11.

The reaction and regeneration zones can be within a single reactor, although better process control usually is achieved if the two are in separate units.

The conversion of acrolein in percent is defined as 100 times the number of mols of acrolein converted, divided by the number of mols of acrolein in the feed. The selectivity to acrylic acid in percent is defined as 100 times the number of mols of acrolein converted to acrylic acid divided by the total number of mols of acrolein converted. The yield of acrylic acid in percent is defined as 100 times the number of mols of acrylic acid formed divided by the number of mols of acrolein in the feed.

As indicated previously, there are a number of molybdenum vanadate type oxidants disclosed in the art as suitable for the oxidation of acrolein to acrylic acid. The process of this invention is not limited to a particular method of making these oxidants, nor to a particular promoter; i.e., oxidants known in the art to contain surface labile oxygen capable of converting acrolein to acrylic acid. It should be further appreciated that other transition metal oxidant system known in the art to promote the oxidation of acrolein to acrylic acid, such as for example but not by way of limitation the iron/antimony metal oxide solids, should be considered equivalent for purposes of the process of the present invention.

The multimetal solids used in the various runs of the Example of this invention were prepared by substantially following the procedure in U.S. Pat. No. 6,107,238 wherein the multimetal solid component was slurried with sufficient polysilicic acid solution to result in typically 10 wt % $SiO_2$ in the final calcined solids along with sufficient colloidal silica solution to result in an additional 30 wt % $SiO_2$ in the final calcined solids prior to spray drying and subsequent calcining. Alternatively, it is envisioned that attrition resistance may be imparted by substantially following the related procedure described in U.S. Pat. No. 4,769,477, particularly the procedure of Example 10. The use of the expression "substantially following the procedures" is not intended as an implication that the same ingredients were employed, but rather that the same general techniques were used to achieve attrition resistance starting with the molybdenum vanadate multimetal solids.

The molybdenum vanadate multimetal starting solids were obtained according to EXAMPLE 1(a) of French patent application 97 02344 filed on Feb. 27, 1997 in the name of Elf Atochem S. A., "Process for Manufacture of Acrylic Acid from Acrolein by Redox Reaction and use of a Solid Mixed Oxide Composition as Redox System in the Said Reaction" now issued in the U.S. as U.S. Pat. No. 6,025,523. These starting solids correspond to the formula: $Mo_{12}V_{4.8}Sr_{0.5}W_{2.4}Cu_{2.2}O_x$; where x is the quantity of oxygen bonded to the other elements and depends on their oxidation state.

The procedure involved 3.6 grams of ammonium paratungstate, 3.0 grams of ammonium metavanadate and 12.4 grams of ammonium heptamolybdate being introduced into 100 grams of water and heated to 100° C. Also, 3.0 grams of copper nitrate and 0.62 grams of strontium nitrate were introduced into 5 grams of water and heated to 100° C. The second solution was added to the first and the resulting slurry was then evaporated to dryness. The solids were precalcined at 225° C. in air to produce the desired precursor. Before calcining 400° C. for 4 hours in air, this solid precursor corresponding to the above formula was then mixed with polysilicic acid solution as described in Example 10 of the U.S. Pat. No. 4,677,084 patent (to impart at least 10 wt % silica, see Run 4 of the example) or mixed with polysilicic acid solution and a colloidal silica solution as described in U.S. patent application Ser. No. 09/088,804 to impart 10% silica from the polysilicic acid and 30% silica from the colloidal silica with the remaining 60% being the molybdenum vanadate multimetal component and further treated to produce the attrition resistant molybdenum vanadate multimetal oxide component of the oxidant mixture.

The following example with several individual runs is presented to more fully demonstrate and further illustrate various individual aspects and features of the present invention. As such the examples are felt to be non-limiting and are meant to illustrate the invention but are not meant to be limiting in any way.

EXAMPLE 1

A recirculating solids reactor system of the type shown in FIG. 1 was used to oxidize acrolein to acrylic acid. The transport bed reactor consisted of a small fluidization section surmounted by a ⅝ inch (1.58 cm) diameter by 10 foot tall (3.048 meter) riser tube. The recirculating solids was transported up the riser tube with the reactant and product gases which are in plug flow. Reactant gas contact times were on the order of 1 to 3 seconds. Isothermal conditions were maintained by an electric furnace. Temperatures were maintained in the range of 200 to 350° C. Reactor pressure was maintained from atmospheric up to 2 psig ($1.4 \times 10^4$ Pa). Riser superficial gas velocity was in the range of 6.6 to 10.5 ft/sec (2 to 3.2 m/sec). Acrolein feed concentration was varied as shown in the tables which follow. Steam feed concentrations were in the range of 0 to 22 mol %. All feed flows were controlled by thermal mass flow controllers. Acrolein and nitrogen were fed either to the fluidization zone or directly to the riser tube (by-passing the fluidization zone).

The solids and the product gas stream were separated in a stripper and a series of cyclones. The stripper was a 4 inch (10 cm) diameter fluidized bed. After disengagement and stripping from the solids, the product off-gas was fed to the product quench/absorption system. Solids contact time in the stripper was in the range of 15 seconds to 10 minutes. From the stripper, the solids were then transported to the regenerator.

The regenerator was a 4.5 inch (10.43 cm) diameter fluidized bed. The solids bed height (solids contact time) in the regenerator was controlled by differential pressure control between the stripper and regenerator. Air was fed to the regenerator to re-oxidize the solids. The solids contact time was in the range of 2 to 12 minutes. The off-gas from the regenerator off-gas was fed to the regenerator quench system after disengagement from the solids in a series of cyclones.

From the regenerator, the oxidized solids were then fed back to the fluidization section of the transport bed reactor. The solids circulation rate was in the range of 10 to 65 kg/hr.

The two off-gas quench systems for the product and regenerator off-gases were of identical design. A recirculating liquid served as a direct contact condenser/absorber for the products. Caustic was used on the product off-gas to absorb organic products and to neutralize the acrylic acid produced. Water was used on the regenerator off-gas.

A hot gas sample stream from the product off-gas was taken to two static water absorbers. The first was used to absorb $C_2/C_3$ aldehydes and acids for quantitative analysis by an off-line gas chromatograph. The second was used as a pre-treatment absorber to remove aldehydes and acids which interfere with the analysis, prior to on-line gas chromatographic analysis of $N_2$, $O_2$, CO and $CO_2$.

The regenerator off-gas was sampled down-stream of the water quench and analyzed for $N_2$, $O_2$, CO and $CO_2$. Reactor performance was determined by on-line gas chromatograph analysis for non-absorbed components in each of the two off-gas streams. Water absorbed products were measured by off-line gas chromatograph analysis of the liquid sample absorber.

The primary process variables in the tables below are abbreviated as follows: Fluid. Bed Temp. ° C. (fluidized bed temperature in ° C.), Acrol./C$_3$H$_6$/streem Feed Conc. mol % (acrolein/propylene/steam feed concentrations in mol %), Gas Cont. Time sec (gas contact time in seconds), Sol. Circ. Rate kg/hr (solids circulation rate in kilograms per hour). The primary responses were measured as key process variables were changed, and are abbreviated in the tables below as follows: Acrol.+C$_3$H$_6$ Conver. (percent acrolein plus propylene conversion), Acryl. Select. % (percent selectivity to acrylic acid reaction product) and Sol. Conv. Ratio (solids conversion ratio, i.e., kg of solids circulated/kg acrolein converted).

The tests were grouped into two sets (Tables 1 and 2 below). The first set (Table 1) included tests where all acrolein feeds were to the riser, while the second set (Table 2) included tests where all acrolein feeds were to the fluidized bed.

For example, run 5 in Table 1 below was done in the ⅝ inch diameter riser described above at about 311° C. and atmospheric pressure. A multimetal oxide molybdenum vanadate solids were made attrition resistant using the process described in U.S. patent application 09/088,804 filed Jun. 2, 1998. The feed to the riser consisted of 17.5 mol % acrolein, 21 mol % steam, and the balance N$_2$ at a feed rate to give a nominal gas residence time in the riser reactor zone of 1.3 seconds. The solids were re-oxidized in the fluidized bed regenerator zone and circulated through the riser at a rate of about 11 kg/hr. The acrolein conversion was 41.5% with a selectivity to acrylic acid of 94.2%.

TABLE 1

| | ALL ACROLEIN FEEDS TO RISER PROCESS VARIABLES | | | | RESPONSES | | |
|---|---|---|---|---|---|---|---|
| Test Num. | Fluid. Bed Temp. ° C. | Acrol./C$_3$H$_6$/steam Feed Conc. mol % | Gas Cont. Time sec | Sol. Circ. Rate kg/hr | Acrol. +C$_3$H$_6$ Conver. % | Acryl. Select. % | Sol. Conv. Ratio kg/kg |
| 1 | 308 | 9.6/0.0/21 | 1.3 | 30 | 58.9 | 90.6 | 297 |
| 2 | 314 | 9.5/0.0/22 | 1.4 | 17 | 72.4 | 92.8 | 139 |
| 3 | 311 | 6.1/0.0/21 | 1.4 | 39 | 72.9 | 85.7 | 507 |
| 4 | 305 | 9.6/0.0/21 | 1.4 | 18 | 63.7 | 90.1 | 165 |
| 5 | 311 | 17.5/0.0/21 | 1.3 | 11 | 41.5 | 94.2 | 87 |
| 6 | 292 | 9.6/0.0/21 | 1.4 | 25 | 66.5 | 92.6 | 219 |
| 7 | 311 | 9.6/3.0/22 | 1.4 | 22 | 51.7 | 93.7 | 201 |
| 8 | 309 | 9.6/6.0/21 | 1.4 | 22 | 31.9 | 89.1 | 274 |
| 9 | 316 | 9.2/5.0/22 | 1.4 | 22 | 47.6 | 91.1 | 185 |

TABLE 2

| | ALL ACROLEIN FEEDS TO RISER PROCESS VARIABLES | | | | RESPONSES | | |
|---|---|---|---|---|---|---|---|
| Test Num. | Fluid. Bed Temp. ° C. | Acrol./C$_3$H$_6$/steam Feed Conc. mol % | Gas Cont. Time sec | Sol. Circ. Rate kg/hr | Acrol. +C$_3$H$_6$ Conver. % | Acryl. Select. % | Sol. Conv. Ratio kg/kg |
| 10 | 267 | 3.3/0.0/4 | 2.2 | 24 | 87.1 | 86.9 | 480 |
| 11 | 271 | 3.7/0.0/0 | 2.2 | 29 | 54.8 | 83.6 | 801 |
| 12 | 262 | 4.1/0.0/0 | 2.2 | 24 | 55.8 | 86.5 | 685 |
| 13 | 268 | 4.3/0.0/10 | 2.1 | 22 | 82.0 | 94.7 | 351 |
| 14 | 266 | 4.4/0.0/19 | 2.1 | 18 | 83.2 | 91.7 | 269 |
| 15 | 262 | 4.5/0.0/20 | 2.1 | 26 | 82.5 | 88.1 | 422 |
| 16 | 263 | 4.5/0.0/20 | 2.2 | 23 | 84.1 | 89.7 | 340 |
| 17 | 250 | 4.5/0.0/20 | 2.2 | 28 | 81.3 | 92.4 | 428 |
| 18 | 265 | 4.5/0.0/20 | 2.1 | 36 | 83.7 | 84.9 | 534 |
| 19 | 256 | 4.5/0.0/20 | 2.2 | 20 | 84.3 | 92.2 | 295 |
| 20 | 263 | 7.6/0.0/20 | 2.2 | 20 | 84.9 | 91.8 | 170 |
| 21 | 308 | 8.7/0.0/20 | 2.0 | 20 | 90.4 | 87.5 | 205 |
| 22 | 270 | 9.1/0.0/20 | 2.1 | 64 | 71.3 | 92.6 | 553 |
| 23 | 304 | 8.6/1.5/21 | 2.0 | 28 | 79.0 | 87.8 | 208 |

The above tests illustrate the good performance obtainable using a transport bed process to convert acrolein to acrylic acid, demonstrating excellent solids activity, selectivity and oxygen carrying capacity. For example, greater than 70% conversion, greater than 92% selectivity was achieved (test 2) with a solids conversion ratio of below 140 kg solids circulated per kg of acrolein converted using 9.5% acrolein in the feed and a riser reactor only 3 meters tall. It should be apparent to one skilled in the art that even better results can be obtained with a higher reactor. The above results further show that there are essentially no disadvantages for feeding propylene with the acrolein.

Having thus described and exemplified the invention with a certain degree of particularity, it should be appreciated that the following claims are not to be so limited but are to be afforded a scope commensurate with the wording of each element of the claim and equivalents thereof.

We claim:

1. A process for the selective vapor phase oxidation of acrolein to acrylic acid in a recirculating solids reactor system using particulate molybdenum vanadate multimetal oxide in oxidized form as oxidant comprising:

(a) contacting a feed gas containing from 1 mol % to 100 mol % acrolein, 0 to 20 mol % oxygen, 0 to 70 mol % water, and the remainder inert gas with an effective amount of an oxidant comprising a particulate molybdenum vanadate multimetal oxide in oxidized form and having a particle size range of 10 to 300 micrometers, in a transport bed reactor at a temperature of about 250 to about 450° C., with a gas residence time in the reaction zone from 1 second to 15 seconds, and with a solids residence time in the reaction zone from 2 seconds to 120 seconds;

(b) removing and recovering acrolein from the effluent gases produced in the transport bed reactor of step (a) by separating the resultant reduced particulate molybdenum vanadate multimetal oxide from the effluent gases;

(c) transporting the reduced particulate molybdenum vanadate multimetal oxide to a regenerator zone of the recirculating solids reactor system;

(d) oxidizing the reduced particulate molybdenum vanadate multimetal oxide in the regenerator zone using an oxygen containing gas, at a temperature of from 250 to 500° C. at a solids residence time in the regenerator zone of from 0.5 minute to 10 minutes, and at an oxygen-containing gas residence time of from 3 seconds to 30 seconds; and (e) recycling the oxidized particulate molybdenum vanadate multimetal oxide from step (d) to the transport bed reactor.

2. A process as claimed in claim 1 wherein said feed gas contains from 5 to 30 mol % acrolein.

3. A process as claimed in claim 1 wherein the transport bed reactor is a riser.

4. A process as claimed in claim 3 wherein the superficial gas velocity in the riser is maintained at 1 to 10 meters/sec.

5. A process as claimed in claim 3 wherein the solids flux (mass flow rate per unit area) is at 5 to 1,000 kg·m$^{-2}$·sec$^{-1}$.

6. A process as claimed in claim 1 wherein the solids regenerator zone is a fluidized bed, and the oxygen-containing gas to the regenerator is air.

* * * * *